(12) United States Patent
Gibson et al.

(10) Patent No.: US 7,026,496 B2
(45) Date of Patent: Apr. 11, 2006

(54) DIAMIDO ALKOXIDES AS POLYMERISATION INITIATORS

(75) Inventors: Vernon Charles Gibson, London (GB); Edward Leslie Marshall, Croydon (GB); Andrew Peter Dove, West Yorkshire (GB)

(73) Assignee: Imperial College Innovations Limited, (GB)

( * ) Notice: Subject to any disclaimer, the term of this patent is extended or adjusted under 35 U.S.C. 154(b) by 0 days.

(21) Appl. No.: 10/416,284

(22) PCT Filed: Nov. 8, 2001

(86) PCT No.: PCT/GB01/04969

§ 371 (c)(1), (2), (4) Date: Jan. 21, 2004

(87) PCT Pub. No.: WO02/38574

PCT Pub. Date: May 16, 2002

(65) Prior Publication Data
US 2005/0004384 A1    Jan. 6, 2005

(30) Foreign Application Priority Data
Nov. 10, 2000    (GB)    ................................ 0027530

(51) Int. Cl.
*C07F 7/22*    (2006.01)
*C07F 5/06*    (2006.01)
*C08G 63/82*    (2006.01)
*C08L 67/06*    (2006.01)

(52) U.S. Cl. .................. 556/81; 556/179; 525/415; 528/357

(58) Field of Classification Search .................. 556/81, 556/179; 528/357; 525/415
See application file for complete search history.

(56) References Cited

FOREIGN PATENT DOCUMENTS

DE    40 28 764 A1    3/1992

OTHER PUBLICATIONS

Duda, Andrzej et al., "Kinetics of epsilon.-caprolactane polymerization on dialkylaluminum alkoxides", Makromol. Chem. Macromol. Symp. 47, 127-140 (1991).

Chang, et al., "Sterically Hindered Aluminum—Magnesium Bridged Complex: {Me2Al[μ-N($^1$C$_3$H$_7$)$_2$]$_2$Mg-[O-2,6-($^1$C$_4$H$_9$)$_2$-4-MeC$_6$H$_2$]}", Inorg. Chem. 1995, vol. 34, No. 17, pp. 4296-4298.

*Primary Examiner*—Porfirio Nazario-Gonzalez
(74) *Attorney, Agent, or Firm*—Fay, Sharpe, Fagan, Minnich & McKee, LLP

(57) ABSTRACT

The present invention relates to a complex having the formula (I) wherein M is selected from Sn(II), Sn(IV), Al(III) and Mg(II); each of $R^1$ and $R^2$ is independently hydrocarbyl; $R^3$ is H or hydrocarbyl; and X is a linker group. A further aspect of the invention relates to the use of said complex as a polymerisation initiator, particularly in the polymerisation of lactides.

29 Claims, 6 Drawing Sheets

DIAMIDO ALKOXIDES AS POLYMERISATION INITIATORS

The present invention relates to a series of discrete, well-defined coordination complexes. More specifically, the invention relates to complexes that are usefull as polymerisation initiators, and in particular, in lactide polymerisation.

Over recent years, there has been an increasing interest in the design of polymers for in vivo applications such as sutures, artificial tissue networks and drug delivery agents. For these applications it is desirable for the polymer to be non-toxic, biocompatible and resorbable. One of the most promising classes of polymer in this field are the poly(lactide)s [J. C. Middleton, A. J. Tipton, Biomaterials, 2000, 21, 2335].

Initiators for lactide polymerisation are typically based on alkoxide or alkanoate complexes of metals such as Al, Mg, Sn, Zn and the rare earths. Tin(II) catalysts such as Sn(ethylhexanoate)$_2$ are generally preferred in the commercial production of poly(lactide)s [E. E. Schmitt and R. A. Rohistina, U.S. Pat. No. 3,297,033, 1967 (Chem. Abstr. 1967, 66, P38656u); E. E. Schmitt and R. A. Rohistina, U.S. Pat. No. 3,463,158, 1969 (Chem. Abstr. 1969, 71, P92382t); H. R. Kricheldorf, I. Kreiser-Saunders and C. Boettcher, Polymer, 1995, 36, 1253, and references therein] for medical or pharmaceutical applications due to the low toxicity of Sn(II) compared to other metal ions. Indeed, Sn(ethylhexanoate)$_2$ is a permitted food additive in many countries.

To date, the ring opening polymerisation of cyclic ethers and esters are usually carried out with the aid of so-called "coordinate catalysts" which are ill-defined with regard to their exact mechanism and structure. In the polymerisation of lactide, the exact structure and detailed mode of reaction of the above-mentioned tin carboxylates, M(O$_2$CR)$_2$, are not fully understood. Indeed, some evidence suggests that the active species in the polymerisation of lactides using tin octanoates may actually be a hydrolysis product, present only as a minor component.

A number of systems that initiate the living ring-opening polymerisation of lactide have been disclosed in the art. By way of example, systems based on aluminium [P. Dubois, C. Jacobs, R. Jérome, P. Teyssié, Macromolecules 1991, 24, 2266; P. A. Cameron, D. Jhurzy, V. C. Gibson, A. J. P. White, D. J. Williams, S. Williams, Macromol. Rapid. Commun. 1999, 20, 616; N. Spassky, M. Wisniewski, C. Pluta, A. LeBorgne, Macromol. Chem. Phys. 1996, 197, 2627], and more recently, magnesium [M. H. Chisholm, N. W. Eilerts, J. Chem. Soc., Chem. Commun., 1996, 853] and zinc [M. Cheng, A. B. Attygalle, E. B. Lobkovsky, G. W. Coates, J. Am. Chem. Soc. 1999, 121, 11583], have all been described.

Another important advance in modern polymer synthesis is the control achievable over the tacticity of polymers derived from prochiral monomers or monomers bearing stereogenic centres. This is most dramatically exemplified by the family of propylenes obtained using ansa-metallocene polymerisation catalysts, leading to materials with new and markedly different properties.

By comparison, relatively little research has been directed towards poly(lactide)s derived from the polymerisation of rac- and meso-lactides, which are the cyclic diesters of lactic acid. These are gaining increasing attention due to their medicinal, pharmaceutical and agricultural applications as well as uses as environmentally benign packaging materials.

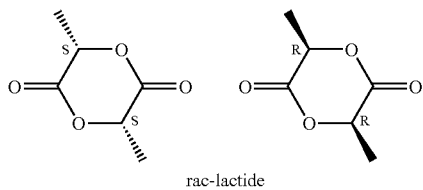

rac-lactide

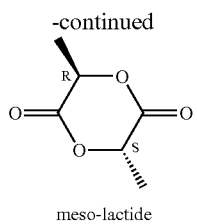

meso-lactide

Unsurprisingly, the physical properties of the poly(lactide)s are also strongly dependent upon their tacticity. For example, isotactic poly(R,R-lactide) is a semi-crystalline thermoplastic of high mechanical strength and toughness (Tg ~57° C., Tm ~174° C.), while syndiotactic poly(R,S-lactide) has a lower softening temperature (Tg ~45° C., Tm ~152° C.) and has found applications in controlled drug release. Atactic poly(lactide), usually obtained upon polymerisation of rac-(R,R/S,S)-lactide is an amorphous polymer with a glass transition temperature near room temperature.

In recent years there have been a number of studies on the stereoselective polymerisation of lactide monomers using single-site catalysts. Spassky and co-workers have described the selective polymerisation of one of the enantiomers of rac-lactide (essentially a kinetic resolution) to isotactic poly(lactide) using a resolved tetradentate Schiff base complex of aluminium [Spassky et al, ibid]. Baker and Smith have shown that a racemic mixture of a similar complex can be used to polymerise both enantiomers of rac-lactide to the isotactic stereocomplex which has the added advantage of possessing a melting point approximately 50° C. higher than the homochiral polymers [C. P. Radano, G. L. Baker, M. R. Smith III, J. Am. Chem. Soc. 2000, 122, 1552]. Moreover, studies on meso-lactide have revealed that syndiotactic poly(lactide) can also be obtained [Cheng et al, ibid]. The aluminium catalyst systems, however, tend to give low rates of propagation, and more highly active catalysts would be beneficial for the commercial production of such materials. A significant development was the recent introduction of a zinc catalyst bearing β-diketininate ligands which acts as a highly efficient catalyst for the polymerisation of rac-lactide to heterotactic poly(lactide) via a chain end control mechanism [Cheng et al, ibid].

The present invention seeks to provide alternative, well-defined, single-site metal complexes that are suitable for use as polymerisation initiators. More specifically, the invention seeks to provide well-defined complexes that are suitable for initiating the polymerisation of lactide.

In a broad aspect, the present invention provides a series of well-defined metal complexes.

More specifically, the invention provides a complex having the formula I

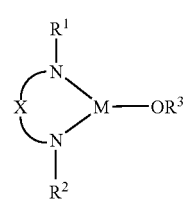

I wherein
M is selected from Sn(II), Sn(IV), Al(III) and Mg(II);
each of R$^1$ and R$^2$ is independently hydrocarbyl;

$R^3$ is H or hydrocarbyl; and

X is a linker group.

Preferably, each of $R^1$, $R^2$ and $R^3$ is independently hydrocarbyl.

As used herein, the term "hydrocarbyl" refers to a group comprising at least C and H that may optionally comprise one or more other suitable substituents. Examples of such substituents may include halo-, alkoxy-, nitro-, an alkyl group, or a cyclic group. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain heteroatoms. Suitable heteroatoms will be apparent to those skilled in the art and include, for instance, sulphur, nitrogen, oxygen, phosphorus and silicon.

In a preferred aspect of the invention, the linker group X comprises a $C_{1-4}$ carbon backbone, or a heteroatom-containing $C_{1-4}$ carbon backbone. Preferably, the linker group X is a $C_2$ or $C_3$ carbon backbone.

In a further preferred aspect of the invention, each of $R^1$ and $R^2$ is independently selected from alkyl, cycloalkyl, haloalkyl, aryl, haloaryl or heteroaryl; and $R^3$ is hydrogen, alkyl, cycloalkyl, haloalkyl, aryl or haloaryl.

As used herein, the term "alkyl" refers to a saturated carbon-containing chain which may be straight or branched, and substituted (mono- or poly-) or unsubstituted. Suitable substituents include those which do not have any significant adverse effect on the activity of the complex as a polymerisation initiator.

Preferably, the alkyl group is a $C_{1-20}$ alkyl group, more preferably a $C_{1-10}$ alkyl group.

Accordingly, the term "haloalkyl" refers to an alkyl group substituted by at least one halogen, for example, chlorine, bromine, fluorine or iodine.

As used herein, the term "aryl" refers to an aromatic, substituted (mono- or poly-) or unsubstituted. Again, suitable substituents include those which do not have any significant adverse effect on the activity of the complex as a polymerisation initiator.

Accordingly, the term "haloaryl" refers to an aryl group substituted by a halogen, for example, chlorine, bromine, fluorine or iodine.

As used herein, the term "cycloalkyl" refers to a cyclic alkyl group.

As used herein, the term "heteroaryl" refers to an aromatic heterocycle comprising one or more heteroatoms. Preferred heteroaryl groups include pyrrole, pyrmidine, pyrazine, pyridine, quinoline and furan.

In a preferred aspect, the linker group X is conjugated.

In one preferred aspect of the invention, the linker group X comprises a vinylene or an arylene group.

In a preferred aspect, the complex of the invention has the formula II,

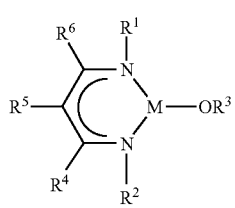

II wherein each of $R^4$, $R^5$ and $R^6$ is independently selected from hydrogen, alkyl, cycloalkyl, haloalkyl, aryl, haloaryl and heteroaryl, and $R^{1-3}$ and M are as defined hereinbefore.

In a more preferred aspect of the invention, each of $R^4$, $R^5$ and $R^6$ is independently selected from H, methyl, t-butyl, phenyl and trifluoromethyl. Even more preferably, $R^5$ is H and $R^4$ and $R^6$ are alkyl, more preferably methyl.

The skilled person will appreciate that where the metal is Al(III), the complex will have an overall charge of 1+, and where the metal is Sn (IV), the ligand will be dianionic and the complex will have an overall charge of 1+. Accordingly, when the metal is Sn(II) or Mg(II), the complex is neutral.

In one particularly preferred aspect, M is Sn(II).

In another particularly preferred aspect, M is Mg(II).

In one particularly preferred embodiment, the complex of the invention has the formula III

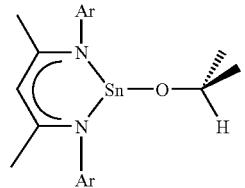

III wherein Ar is o-diisopropylphenyl.

In contrast to the ill-defined tin "coordinate catalysts" of the prior art, the present invention provides a tin complex with a well-defined structure that is suitable for use as a polymerisation initiator.

The complex of formula III is prepared according to the scheme shown in FIG. 1. Treatment of $SnCl_2$ with [HC{C(Me)NAr}$_2$]Li in diethylether followed by crystallisation from pentane affords [HC{C(e)NAr}$_2$]SnCl, IIIa as a yellow crystalline solid. This is converted to III by treatment with LiOPr$^i$ followed by re-crystallisation from pentane. Crystals of III suitable for an X-ray structure determination were grown from pentane; the structure is shown in FIG. 2. Further details of the X-ray structure may be found in the accompanying examples.

The complex of formula III has non-crystallographic CS symmetry with the three-coordinate tin atom adopting a tripodal geometry with inter-bond angles in the range 83.6(2)–94.1(2)°, the most acute being associated with the bite of the chelating N,N' ligand. The Sn—N and Sn—O distances are unexceptional, and there is the expected pattern of delocalisation within the β-diketiminate ligand. The six-membered chelate ring has a boat conformation with C(2) and Sn lying 0.12 and 0.87 Å "above" the N(1), C(1), C(3), N(3) plane; the isopropoxide oxygen atom lies 0.74 Å "below" this plane. As a consequence of the folded chelate ring conformation, and retention of near trigonal planar geometries at the two nitrogen centres, the C(12) and C(27) isopropyl groups are drawn together, and those associated with C(15) and C(24) are folded away exposing the non-coordinated "face" containing the stereochemically active lone pair on the tin atom; the shortest intermolecular approach to the tin centre is 3.84 Å from C(13)—H.

A further aspect of the present invention relates to the use of the above-described complexes as polymerisation initiators.

As used herein, the term "polymerisation initiator" refers to an agent used to start the polymerisation of a monomer.

In a preferred aspect, the invention relates to the use of the complexes described herein as initiators in the polymerisation of lactide. The term "lactide" encompasses rac-lactide, meso-lactide and the resolved L and D forms of lactide.

In particular, the complexes of the invention may be used as initiators in the "living polymerisation" of lactide. As used herein, the term "living polymerisation" refers to a polymerisation in which there is no termination step, i.e. the initiator complex is associated with the end of the propagating polymer chain and is not released.

Even more preferably, the lactide is in the form of rac-lactide. As used herein, the term "rac-lactide" refers to a racemic mixture of L (S,S) and D (R,R) lactide.

By way of example, the polymerisation of rac-lactide was initially investigated using complex III in $CH_2Cl_2$ at ambient temperature. Under these conditions it was found that 100 equivalents of monomer required 96 hours for complete conversion (>99% by $^1H$ NMR). The resultant polymer has a molecular weight close to that calculated from the monomer:initiator ratio (observed $M_n$=17,100; calculated $M_n$=14,400) and exhibits a narrow polydispersity ($M_w/M_n$=1.11), characteristics of a living process. The polymerisation was then repeated at 60° C. in toluene affording 85% conversion after 4 hours, again resulting in a narrow molecular weight distribution product ($M_w/M_n$=1.05). The activity of the tin catalyst is lower than that observed for the related zinc system [Cheng et al, ibid] which may be in part due to the lower electrophilicity of the tin centre, and partly a consequence of the stereochemically active lone pair which may disfavour monomer binding. The living characteristics of the polymerisation are confirmed by the linear increase in $M_n$ with conversion giving in each case a low polydispersity product (FIG. 3).

In order to confirm that the initiator is indeed the iso-propoxide complex III, a $^1H$ NMR study was carried out in which increasing amounts of lactide were added to III in $CDCl_3$. The iso-propoxide methine septet resonance at the end of the propagating chain is shifted slightly to higher frequency (0.005 ppm) relative to the unconsumed initiator (δ4.01). New resonances for the β-diketiminate ligand substituents are also observed for the propagating species. As the number of monomer equivalents is increased, the intensities of the signals attributable to the propagating species increase relative to those of unconsumed III. Due to the overlapping nature of the resonances, accurate integration has not been possible, but the addition of 5 equivalents of monomer leads to an approximately 1:1 mixture of initiator: propagating species. This indicates a favourable kp/ki ratio (the rate constant of propagation to rate constant of initiation) which is desirable for minimising the polydispersity.

The $^1H$ NMR spectrum of the poly(lactide) derived from m (FIG. 4) differs from the spectrum predicted from a Bernouillian analysis of totally random poly(rac-lactide), with the rmr and mrm tetrads much more intense than expected. These observations are consistent with a heterotactic-biased product since the rmr microstructure can only arise from two consecutive D-L or L-D interchanges; each rmr tetrad is accompanied by two mrm tetrads in agreement with the NMR integration. This represents the first example of tacticity bias arising from the polymerisation of rac-lactide using a tin catalyst.

As used herein, the term "heterotactic" refers to a polymer in which the adjacent monomer units alternate in the form [-L-D-L-D-L-D . . . ]. A true heterotactic polymer is one in which the monomer units alternate perfectly in this fashion. A polymer exhibiting a "heterotactic bias" therefore refers to a polymer in which there is a bias towards heterotacticity, compared to an "atactic" polymer in which there is no regular arrangement of monomer units along the chain.

In another particularly preferred embodiment, the complex of the invention has the formula IV

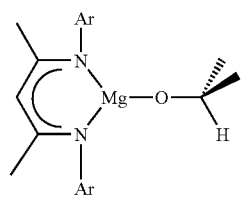

IV wherein Ar is o-diisopropylphenyl.

In one preferred embodiment, the complex of the invention has the formula V

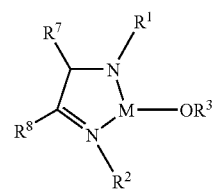

V wherein $R^{1-3}$ and M are as defined hereinabove, and wherein each of $R^7$ and $R^8$ is independently selected from H, alkyl, cycloalkyl, haloalkyl, aryl, haloaryl and heteroaryl.

Preferably, each of $R^7$ and $R^8$ is independently selected from H and alkyl, more preferably, H and methyl.

In one particularly preferred embodiment, $R^7$ is H and $R^8$ is methyl.

Even more preferably, the complex has the formula VI

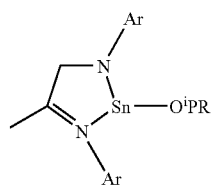

VI wherein Ar is o-diisopropylphenyl.

In a further preferred aspect, the complex of the invention comprises a dimer of a complex as described herein.

Preferably, the dimer has the formula VII

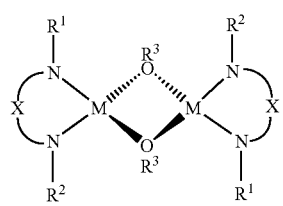

VII

In a particularly preferred embodiment of the invention, the complex has the formula VIII

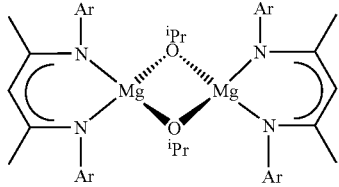

VIII

The complex of formula VIII is prepared according to either of the two procedures outlined in FIG. 5. Reaction of dimethyl magnesium with 2-(2,6-di-iso-propylphenylamino)-4-(2,6-di-iso-propylphenylimino)-2-pentene in toluene affords the bridged methyl dimer, VIIIa. Alcoholysis proceeds smoothly upon addition of 2 equivalents of $^i$PrOH in toluene, to give the bridged alkoxide species, VIII. Alternatively, VIII may be prepared by stirring a toluene solution of [HC(CMeNAr)$_2$]Mg$^i$Pr, VIIIb, under a dioxygen atmosphere.

The crystal structure of complex VIII is shown in FIG. 6. Both magnesium centres exhibit a distorted tetrahedral geometry (N—Mg—N=92°; O—Mg—O=81°).

Recent studies by the applicant have investigated the synthesis of a range of magnesium alkyl complexes bearing the β-diketiminate ligand [V. C. Gibson, J. A. Segal, A. J. P. White, D. J. Williams, J. Am. Chem. Soc. 2000, 122, 7120]. The present invention discloses that the alkoxide derivatives of these magnesium complexes, as described herein are, in fact, highly effective catalysts for the living polymerisation of lactide.

Yet another aspect of the invention relates to a process for the polymerisation of lactide, said process comprising contacting an initiating amount of a complex according to the invention with lactide monomer in the presence of a suitable solvent.

As used herein, the term "initiating amount" refers to a sufficient amount of an initiator to commence the chemical reaction of polymerisation.

In a preferred aspect, the ratio of lactide monomer to the initiator complex of the invention is between 100:1 and 20000:1.

By way of example, suitable solvents include dichloromethane and toluene. Other solvents suitable for the purposes of the present invention will be familiar to those skilled in the relevant art.

A further aspect of the invention relates to an article produced by the process described hereinbefore.

Preferably, the article is a medical article. Typical articles may include sutures, drug delivery devices and medical implants, for example, orthopedic fixation devices.

Yet another aspect of the invention provides a process for preparing a complex of formula I, said process comprising the steps of:

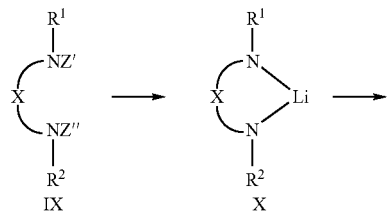

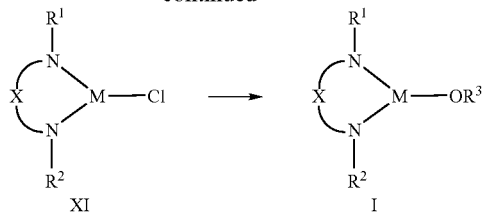

(i) reacting a compound of formula IX, wherein each of Z' and Z" is independently H (where —NR$^1$ and/or —NR$^2$ is an amino group) or absent (where —NR$^1$ and/or —NR$^2$ is an imino group), with $^n$BuLi to form a compound of formula X;

(ii) reacting said compound of formula X with MCl$_n$ to form a compound of formula XI, wherein M is selected from Sn(II), Mg(II), Al(III) and Sn(IV) and n is 2, 2, 3 or 4 respectively;

(ii) reacting said compound of formula XI with LiOR$^3$ to form a complex of formula I;

wherein X and R$^{1-3}$ are as defined hereinbefore.

Another aspect of the invention relates to a process for preparing a complex of formula XIII, said process comprising the steps of:

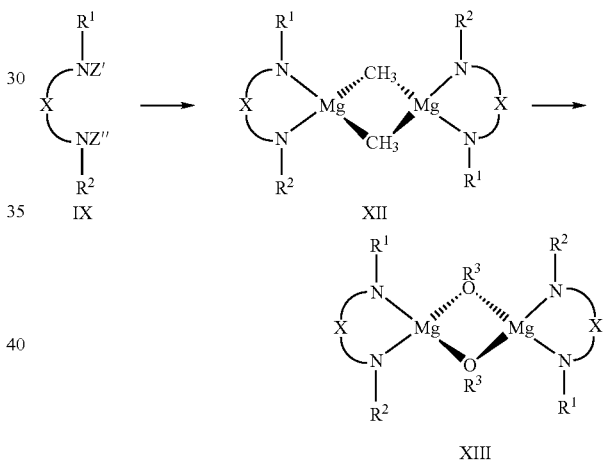

(i) reacting a compound of formula IX, wherein each of Z' and Z" is independently H (where —NR$^1$ and/or —NR$^2$ is an amino group) or absent (where —NR$^1$ and/or —NR$^2$ is an imino group), with MgMe$_2$ to form a compound of formula XII;

(ii) reacting said compound of formula XII with R$^3$OH to form a compound of formula XIII;

wherein X and R$^{1-3}$ are as defined hereinbefore.

A further aspect of the invention provides a process for preparing a complex of formula XIII, said process comprising the steps of:

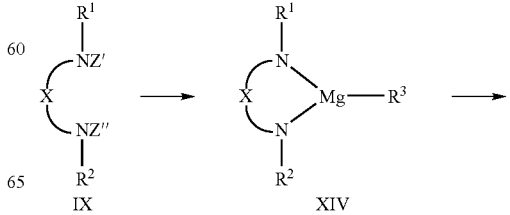

-continued

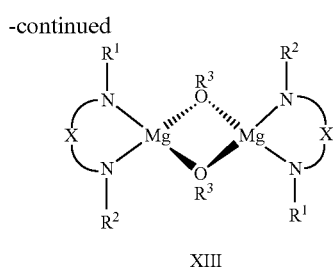

XIII (i) reacting a compound of formula IX, wherein each of Z' and Z" is independently H (where —NR$^1$ and/or —NR$^2$ is an amino group) or absent (where —NR$^1$ and/or —NR$^2$ is an imino group), with (a) "BuLi and (b) R$^3$MgCl to form a compound of formula XIV;

(ii) reacting said compound of formula XIV with O$_2$ to form a complex of formula XIII;

wherein X and R$^{1-3}$ are as defined hereinbefore.

The present invention will now be described by way of example and with reference to the following figures wherein:

FIG. 1 shows the reaction scheme for the preparation of the Sn(II) complex III.

FIG. 2 shows the molecular structure of complex III. In more detail, the selected bond lengths (Å) and angles (°) in the molecular structure of III are as follows; Sn—O 2.000 (5), Sn—N(1) 2.206(4), Sn—N(3) 2.208(4), C(1)-N(1) 1.323(6), C(1)-C(2) 1.404(7), C(2)-C(3) 1.387(7), C(3)-N (3) 1.331(6), O—Sn—N(1) 94.1(2), O—Sn—N(3) 92.5(2), N(1)-Sn—N(3) 83.6(2).

EXAMPLES

Synthesis of [HC{C(Me)NAr}$_2$]SnCl, Complex IIIa

Figure 1:
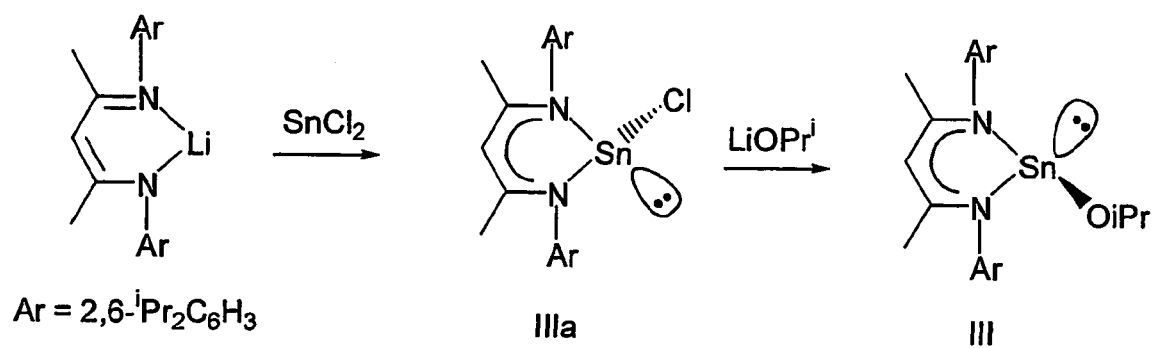
Figure 2:
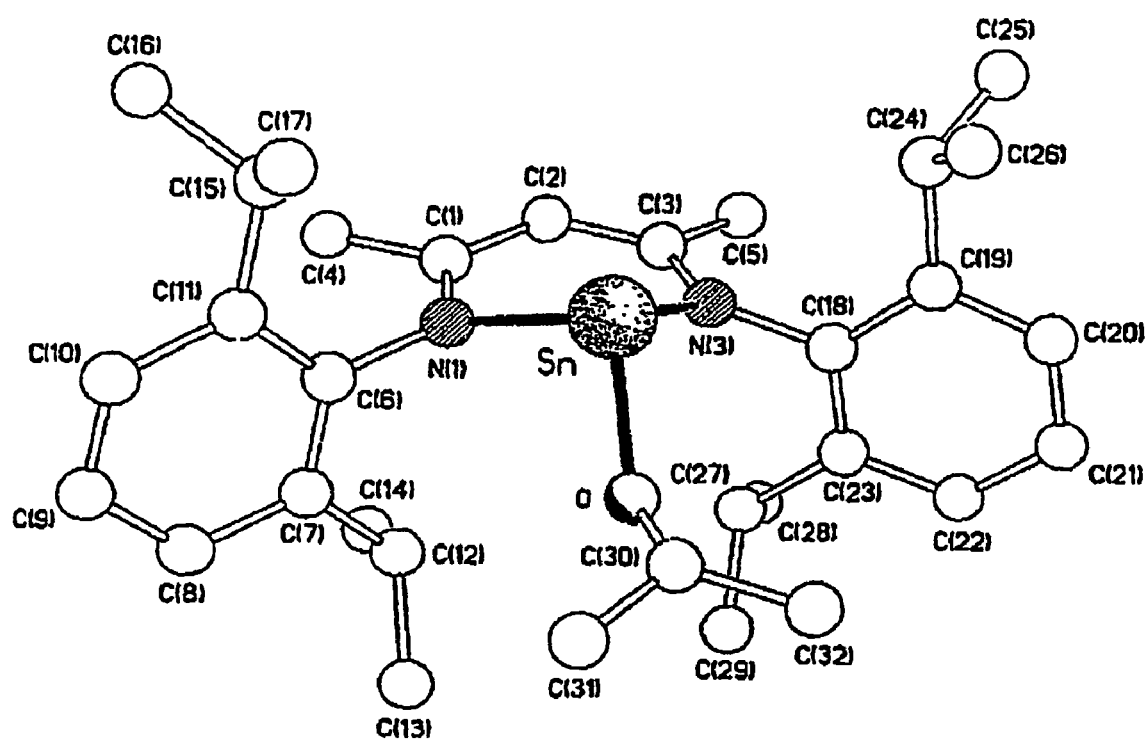
Figure 3:
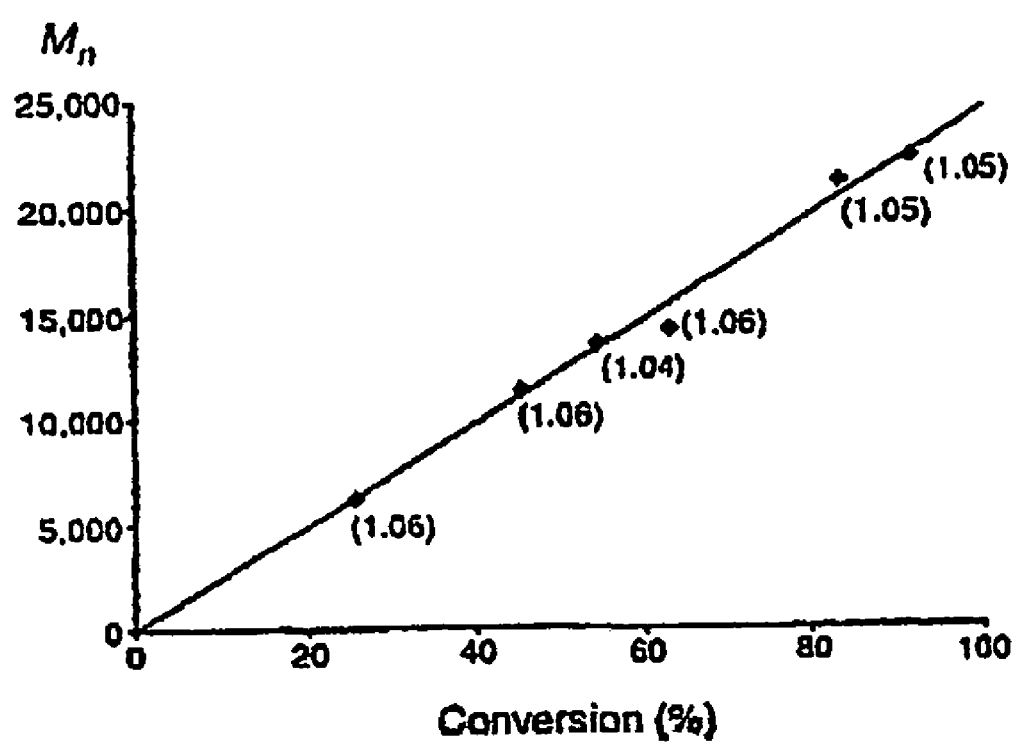
FIG. 3 shows M$_n$ of the resulting polymer against the percentage conversion. In particular, FIG. 3 confirms the living characterisitics of polymerisation, showing a linear increase in M$_n$ with conversion, giving a low polydispersity product.
Figure 4:
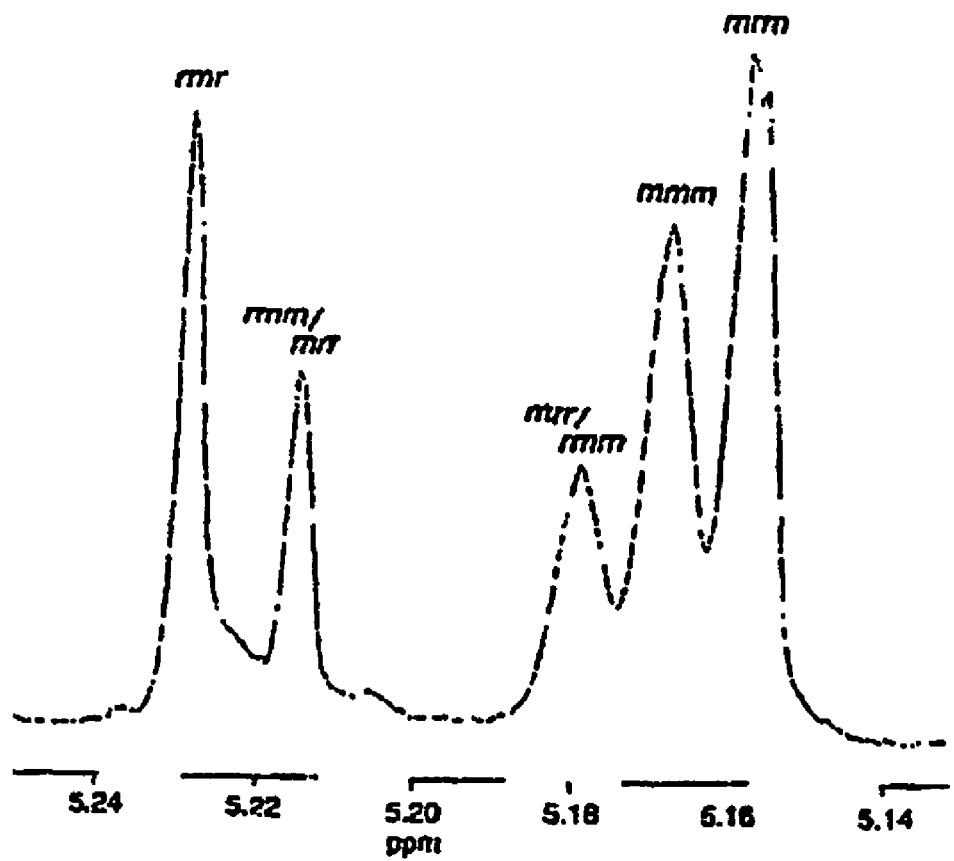
FIG. 4 shows the $^1$H NMR spectrum of the poly(lactide) derived from III.
Figure 5:
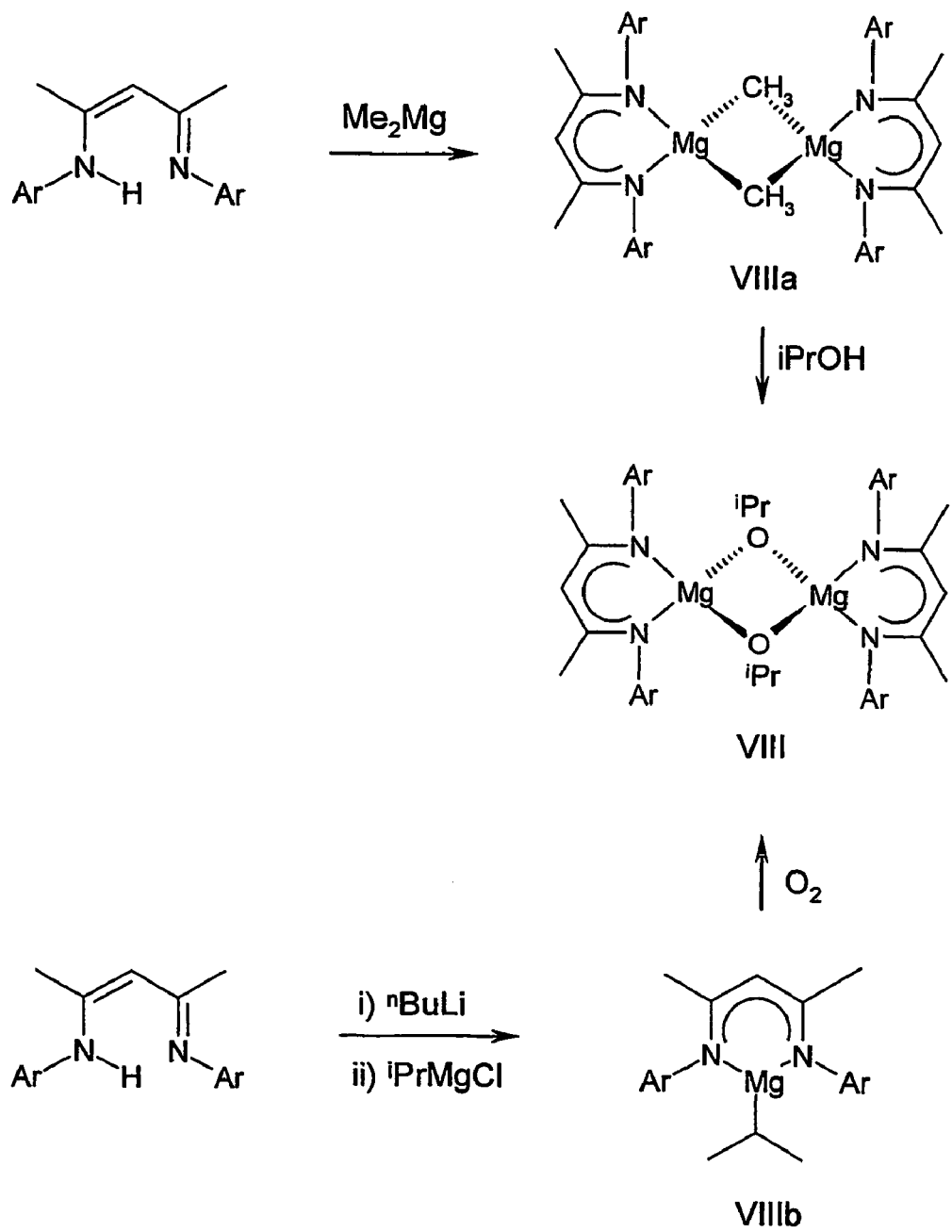
FIG. 5 shows the reaction scheme for the preparation of the magnesium (II) complex VIII.
Figure 6:
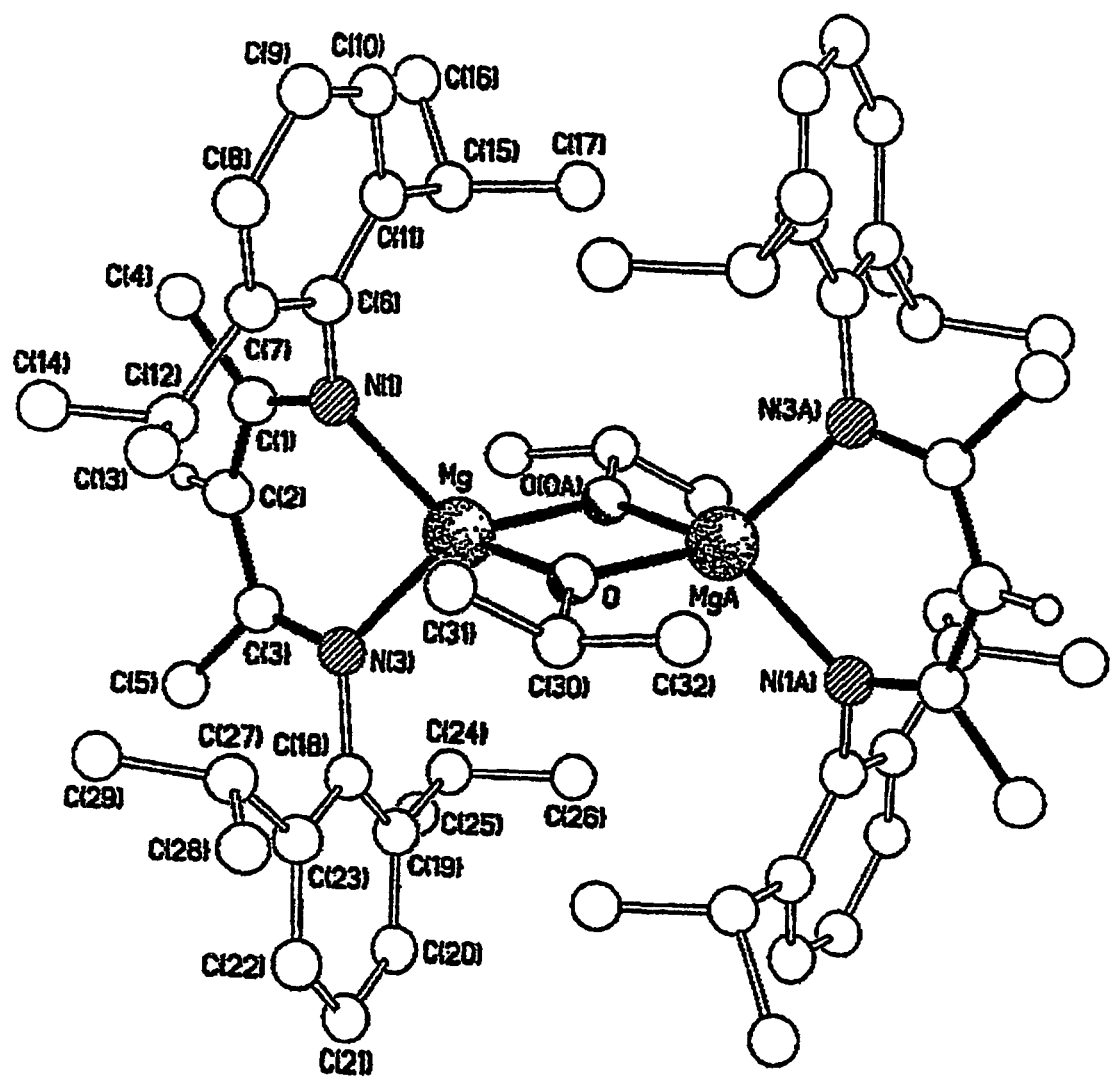
FIG. 6 shows the crystal structure of the magnesium (II) complex VIII.

To a 75 cm$^3$ Et$_2$O solution of 5.00 g ArN═C(Me)CH═C (Me)NHAr (1.19 mmol) at 0° C. was added 7.5 cm$^3$ n-BuLi (1.6M in hexanes; 1.20 mmol). After stirring at room temperature for 16 hours the mixture was added to a 40 cm$^3$ Et$_2$O suspension of SnCl$_2$ (2.26 g; 1.19 mmol) and the reaction was then stirred for 18 hours. Removal of volatiles in vacuo afforded a yellow-orange solid which was recrystallised from cold pentane as pale yellow crystals (3.70 g; 0.72 mmol; 60%).

Spectroscopic Data

Complex IIIa: $^1$H NMR (250 MHz, C$_6$D$_6$, 25° C.) δ 1.06 (d, 6H, $^3$J$_{HH}$=6.8 Hz, CHMeMe), 1.18 (d, 6H, $^3$J$_{HH}$=6.9 Hz, CHMeMe), 1.22 (d, 6H, $^3$J$_{HH}$=6.8 Hz, CHMe'Me'), 1.45 (d, 6H, $^3$J$_{HH}$=6.6 Hz, CHMe'Me'), 1.61 (s, 6H, HC{C(Me) NAr}$_2$), 3.12 (sept, 2H, $^3$J$_{HH}$=6.8 Hz, CHMe$_2$), 3.95 (sept, 2H, $^3$J$_{HH}$=6.8 Hz, CHMe$_2$), 5.06 (s, 1H, HC{C(Me)NAr}$_2$), 7.15 (m, 6H, H$_{aryl}$). MS: m/z 572 [M]$^+$. Anal. Calc. (found) for C$_{29}$H$_{41}$ClN$_2$Sn: C, 60.91 (60.77); H, 7.22 (7.32); N, 4.90 (5.07).

Synthesis of [HC{C(Me)NAr}$_2$]Sn(O$^i$Pr), Complex III

Lithium iso-propoxide (0.4365 g, 7.27 mmol) in 70 cm$^3$ toluene was added to a rapidly stirred solution of [HC{C (Me)NAr}$_2$]SnCl (2.0811 g, 3.64 mmol) in 50 cm$^3$ toluene at 0° C. After 18 hours stirring at ambient temperature volatiles were removed to afford a bright yellow solid which was recrystallised from heptane at −30° C. (1.8857 g, 3.16 mmol, 87%).

Spectroscopic Data

Complex III: $^1$H NMR (250 MHz, C$_6$D$_6$, 25° C.) δ 0.90 (d, 6H, $^3$J$_{HH}$=6.8 Hz, OCHMe$_2$), 1.14 (d, 3H, $^3$J$_{HH}$=6.8 Hz, CHMeMe), 1.24 (d, 3H, $^3$J$_{HH}$=6.9 Hz, CHMeMe), 1.27 (d, 3H, CHMe'Me'), 1.54 (d, 3H, CHMe'Me'), 1.59 (s, 6H, HC{C(Me)NAr}$_2$), 3.25 (sept, 2H, $^3$J$_{HH}$=6.8 Hz, CHMe$_2$), 3.86 (sept, 2H, $^3$J$_{HH}$=6.8 Hz, CHMe$_2$), 4.15 (sept, 1H, $^3$J$_{HH}$=6.0 Hz, OCHMe$_2$), 4.73 (s, 1H, HC{C(Me)NAr}$_2$), 7.16 (m, 6H, H$_{aryl}$). Anal. Calc. (found) for C$_{32}$H$_{48}$N$_2$OSn: C, 64.55 (64.28); H, 8.13 (8.08); N, 4.70 (4.90).

Crystallographic Data for Complex III

C$_{32}$H$_{48}$N$_2$OSn, M=595.4, monoclinic, space group P2$_1$/n (no. 14), a=13.205(2), b=16.680(2), c=15.527(2) Å, β=107.42(1)°, V=3263.1(6) Å$^3$, Z=4, D$_c$=1.212 g cm$^{-3}$, μ(Mo—Kα)=8.07 cm$^{-1}$, T=293 K, yellow blocks; 5742 independent measured reflections, F$^2$ refinement, R$_1$=0.049, wR$_2$=0.112, 4038 independent observed reflections [|F$_o$|>4σ (|F$_o$|), 2θ≤50°], 326 parameters.

Synthesis of [{HC(CMeNAr)$_2$}Mg(O$^i$Pr)]$_2$ Complex VIII

Route A 0.15 cm$^3$ propan-2-ol (1.96×10$^{-3}$ mol) was added dropwise to a solution of [{HC(CMeNAr)$_2$}MgMe]$_2$ (1.001 g, 1.067×10$^{-3}$ mol in 50 cm$^3$ toluene). The reaction was then stirred for 60 minutes at room temperature, during which time a white precipitate formed which was recovered by filtration (0.410 g, 0.400×10$^{-3}$ mol, 37.5%). Crystals suitable for x-ray diffraction studies were grown from benzene.

Route B

A schlenk tube containing 0.604 g {HC(CMeNAr)$_2$}Mg ($^i$Pr) (1.215×10$^{-3}$ mol) dissolved in 15 cm$^3$ toluene under a dinitrogen atmosphere was evacuated and an atmosphere of dioxygen was then introduced. The evacuation/refill cycle was repeated a total of three times. Almost immediately the solution turns cloudy, with more precipitate forming during the time-scale of the reaction.

After 30 minutes stirring a room temperature the solution was filtered to afford a white solid.

Spectroscopic Data

Complex VIII: $^1$H NMR δ (CDCl3, 250 MHz): 0.15 (d, 6H, $^3$J$_{HH}$=6.84 Hz, OCHMe2), 0.94 (d, 3H, $^3$J$_{HH}$=6.58 Hz, CHMeMe), 1.02 (d, 3H, $^3$J$_{HH}$=6.58 Hz, CHMeMe), 1.03 (d, 3H, $^3$J$_{HH}$=6.58 Hz, CHMe'Me'), 1.26 (d, 3H, $^3$J$_{HH}$=6.58 Hz, CHMe'Me'), 1.42 (s, 6H, Me$_α$), 2.89 (sept, $^3$J$_{HH}$=6.84 Hz, CHMeMe), 3.28 (sept, $^3$J$_{HH}$=6.84 Hz, CHMe'Me'), 3.63 (sept, $^3$J$_{HH}$=6.84 Hz, OCHMe$_2$), 4.77 (s, 1H, H$_β$), 7.11 (m, 6H, H$_{aryl}$). Anal. Calc. for C$_{70}$H$_{102}$N$_4$Mg$_2$O$_2$: C 77.83, H 9.52, N 5.19%. Found C 77.18, H 9.27, N 5.78%.

Crystallographic data for Complex VIII

The crystallographic data for Complex VIII is attached in Annex 1.

Synthesis of (NN)Sn(O$^i$Pr), Complex VI (NN)Sn(O$^i$Pr) was prepared by the synthetic scheme shown below.

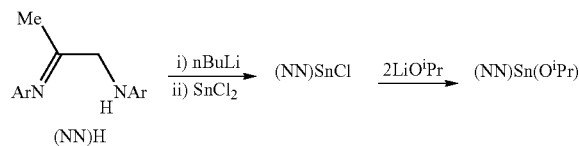

Synthesis of 3-(N-(2,6-di-iso-propylphenlamino)-2-(N-(2,6-di-iso-propylphenyl)imino)propane, (NN)H 86.5 g of ArNCHCHNAr (0.230 mol) was dissolved in 300 cm$^3$ toluene. To this solution a 2.0 M toluene solution of Me$_3$Al (120 cm$^3$, 0.240 mol) was added dropwise over 30 minutes at room temperature, furnishing a deep red colouration.

The reaction was stirred at 80° C. for 16 hours, then chilled in a solid CO$_2$/acetone bath at −78° C. The product, [{ArN═C(Me)CH$_2$NAr}AlMe$_2$], was then slowly hydrolysed by the addition of 200 cm$^3$ degassed, distilled water. The resultant suspension was filtered and the organic layer decanted under nitrogen. The aqueous layer was extracted with 3×50 cm$^3$ portions of diethyl ether. The ether extracts were combined with the toluene solution and dried over anhydrous MgSO$_4$. This mixture was then filtered and volatiles removed in vacuo to give a viscous yellow oil, which solidifies under prolonged vacuum.

Spectroscopic Data (NN)H: $^1$H NMR (C$_6$D$_6$, 250 MHz, 298K): 7.20–7.11 (m, 6H) H$_{meta}$ and H$_{para}$, 5.24 (t, $^3$J$_{HH}$=4.6 Hz, 1H)NH, 3.70 (d, $^3$J$_{HH}$=4.7 Hz, 2H)NCH$_2$, 3.59 (sept, 2H) and 2.85 (sept, 2H) CHMe$_2$, 1.29 (d, 12H), 1.19 (d, 6H), 1.12 (d, 6H), all CHMe$_2$, 1.24 (s, 3H) N═C(Me)

Synthesis of (NN)Li

Handling difficulties associated with the oily nature of (NN)H may be overcome by converting it into its lithium salt, a pale yellow powder, which can be readily recrystallised from hot hydrocarbon solvents (e.g. heptane, toluene).

45.46 g (NN)H (0.118 mol) was dissolved in 200 cm$^3$ Et$_2$O and chilled in a solid CO$_2$/acetone bath at −78° C. To this stirring solution was added 50 cm$^3$ $^n$BuLi (2.5M in hexanes, 0.125 mol) dropwise over 20 minutes. After stirring at room temperature for 3 hours the reaction mixture was filtered and the precipitate washed with 2×50 cm$^3$ pentane. Yield: 42.92 g 93%.

Spectroscopic Data (NN)Li: $^1$H NMR (d$_8$-THF, 250 MHz, 298K): 7.16–6.91 (m, 3H), 6.72 (m, 2H), 6.27 (m, 1H) H$_{meta}$ and H$_{para}$, 4.57 (s, 2H) NCH$_2$, 3.49 (sept, 2H) and 3.04 (sept, 2H) CBMe$_2$, 1.65 (s, 3H) N═C(Me),1.17 (d, 6H), 1.15 (d, 6H), 1.14 (d, 12H), all CHMe$_2$.

Synthesis of (NN)SnCl

A 50 cm$^3$ Et$_2$O solution of (NN)Li (1.4680 g, 3.68×10$^-$3mol) was added to a 30 cm$^3$ Et$_2$O suspension of 0.6983 g SnCl$_2$ (3.68×10$^{-3}$ mol) at −78° C. The mixture was allowed to reach room temperature and then stirred for 2 hours to afford a pale yellow suspension. The reaction was filtered and concentrated in vacuo to give a pale yellow solid. Recrystallisation from Et$_2$O gave a pale yellow crystalline material. Yield: 1.192 g, 59%.

Spectroscopic Data (NN)SnCl: $^1$H NMR (C$_6$D$_6$, 250 MHz, 298K): δ 7.22–7.00 (m, 6H) H$_{meta}$ and H$_{para}$, 4.65 (s, br, 2H) NCH$_2$, 3.89 (br, 2H) and 3.19 (sept, 2H) CHMe$_2$, 1.35 (d, 6H), 1.34 (d, 6H), 1.30 (d, 6H), 1.10 (d, 6H) all CHMe$_2$, 1.21 (s, 3H) N═C(Me)

Synthesis of (NN)Sn(O$^i$Pr). Complex VI 1.1427 g (NN)SnCl and 0.2765 g Li(O$^i$Pr) (2.094×10$^-$3mol and 4.187×10$^{-3}$ mol respectively; 2.00 equivalents) were weighed into a schlenk tube and chilled in a solid CO2/acetone bath at −78° C. 20 cm$^3$ of Et$_2$O was added and the stirring mixture was allowed to warm to room temperature, affording an orange-brown suspension. This was stirred for a further 30minutes, filtered and concentrated under reduced pressure to a sticky orange solid. The solid was purified by stirring in 5 cm$^3$ pentane at −78° C. for 1hour. Yield: 0.417 g, 35%.

Typical Polymerisation Procedure

Using [{HC(CMeNAr)$_2$}Mg(O$^i$Pr)]$_2$ as an Initiator (Complex VIII)

200 equivalents of rac-lactide (0.121 g, 0.840×10$^3$ mol, previously recrystallised from ethyl acetate) were dissolved in 2 cm$^3$ CH$_2$Cl$_2$, and this solution was chilled to −30° C. It was then added to a 2 cm$^3$ CH$_2$Cl$_2$ solution of [{HC(CMeNAr)}$_2$Mg(O$^i$Pr)]$_2$ (0.0043 g, 0.419×10$^{-6}$ mol; [M]/[I] =100) also at −30° C. The reaction mixture was then stirred for the allotted time period, then opened to the atmosphere to destroy the initiator.

The reaction mixture was then reduced in vacuo to afford a sticky white oil, which was analysed by $^1$H NMR to determine conversion. The oil was purified by dissolving in 2 cm$^3$ CH$_2$Cl$_2$ and then reprecipitating from excess cold MeOH.

Using (NN)Sn(O$^i$Pr) as an Initiator (Complex VI)

0.0057 g (NN)Sn(O$^i$Pr) (1.00×10–5 mol) and 0.2885 g rac-lactide (2.00×10$^{-3}$; 200 equivalents) were weighed into an ampoule and 4 cm$^3$ toluene was added. The ampoule was then placed in an oil-bath at 60° C. and stirred for 60 minutes. The polymerisation was terminated by opening the ampoule to air. Volatiles were removed under reduced pressure to yield a cream-coloured foamy solid.

$^1$H NMR spectroscopy confirms that the conversion of lactide to poly(lactide) is 40% (i.e. 80 equivalents of monomer consumed in 60 minutes). GPC (CHCl$_3$): Mn=4.980, Mw=6110, pdi=1.23.

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in chemistry or related fields are intended to be within the scope of the following claims.

TABLE 1

| Crystal data and structure refinement for 1. | |
|---|---|
| Identification code | VG0059 |
| Empirical formula | C$_{64}$H$_{96}$N$_1$O$_2$Mg$_2$ phH |
| Formula weight | 1080.18 |
| Temperature | 203 (2) k |
| Diffractometer Used | Siemens P4/RA |
| Wavelength | 1.54178 A |
| Crystal system | Monoclinic |

TABLE 1-continued

Crystal data and structure refinement for 1.

| | |
|---|---|
| Space group | P2$_1$/n |
| Unit cell dimensions | a = 13.5668 (8) Å  alpha = 90° |
| | b = 16.1541 (8) Å  beta = 98.339 (4)° |
| | c = 14.8933 (7) Å  gamma = 90° |
| Volume, Z | 3229.5 (3) Å$^3$, 2 |
| Density (calculated) | 1.111 Mg/m$^3$ |
| Absorption Coefficient | 0.674 mm$^{-1}$ |
| F (000) | 1180 |
| Crystal colour/morphology | Clear prisms |
| Crystal size | 0.40 × 0.33 × 0.27 mm |
| θ range for data collection | 1.06 to 59.99° |
| Limiting indices | −15 ≦ h < 0, 0 ≦ k < 18 |
| | −16 ≦ l ≦ 16 |
| Scan type | ω-scans |
| Reflections collected | 5027 |
| Independent reflections | 4800 (R$_{int}$ 0.1057) |
| Observed reflections [F > 4σ (F)] | 4066 |
| Absorption correction | None |
| Structure solution method | Direct |
| Refinement method | Full matrix least-squares on F$^2$ |
| Data/restraints/parameters | 4632/0/353 |
| Goodness-of-fit on F$^2$ | 1.023 |
| Final R indices [F > 4σ (F)] | R1 = 0.0498, wR2 = 0.1298 |
| R indices (all data) | R1 = 0.0596, wR2 = 0.1401 |
| Extinction coefficient | 0.00024 (3) |
| Largest diff peak and hole | 0.330 and −0.369 eÅ$^3$ |
| Mean and maximum shift/error | 0.000 and 0.000 |

TABLE 3

Bond lengths [A] and angles [°] for 1.

| | | | |
|---|---|---|---|
| Mg—O | 1.9803 (14) | Mg.O#1 | 1.9863 (14) |
| Mg—N(1) | 2.114 (2) | Mg—N(3) | 2.126 (2) |
| Mg—Mg#1 | 3.0138 (12) | O—C(30) | 1.425 (2) |
| O—Mg#1 | 1.9863 (14) | C(1)—N(1) | 1.339 (3) |
| C(1)—C(2) | 1.102 (3) | C(1)—C(4) | 1.516 (3) |
| N(1)—C(6) | 1.416 (3) | C(2)—C(3) | 1.404 (3) |
| C(3)—N(3) | 1.331 (3) | C(3)—C(5) | 1.523 (3) |
| N(3)—C(18) | 1.451 (2) | C(6)—C(7) | 1.407 (3) |
| C(6)—C(11) | 1.116 (3) | C(7)—C(8) | 1.381 (3) |
| C(7)—C(12) | 1.520 (4) | C(8)—C(9) | 1.387 (5) |
| C(9)—C(10) | 1.375 (5) | C(10)—C(11) | 1.393 (3) |
| C(11)—C(15) | 1.507 (4) | C(12)—C(14) | 1.529 (4) |
| C(12)—C(13) | 1.529 (3) | C(15)—C(17) | 1.523 (3) |
| C(15)—C(16) | 1.530 (1) | C(18)—C(19) | 1.403 (3) |
| C(18)—C(23) | 1.405 (3) | C(19)—C(20) | 1.394 (3) |
| C(19)—C(24) | 1.517 (3) | C(20)—C(21) | 1.373 (3) |
| C(21)—C(22) | 1.372 (4) | C(22)—C(23) | 1.401 (3) |
| C(23)—C(27) | 1.519 (3) | C(24)—C(26) | 1.525 (4) |
| C(24)—C(25) | 1.530 (3) | C(27)—C(29) | 1.521 (4) |
| C(27)—C(28) | 1.527 (3) | C(30)—C(31) | 1.498 (3) |
| C(30)—C(32) | 1.511 (3) | | |
| O—MgO#1 | 81.11 (6) | OMg—N(1) | 125.90 (7) |
| O#1-MgN(1) | 117.94 (6) | O—MgN(3) | 123.28 (6) |
| O#1 Mg—N(3) | 120.75 (7) | N(1)—MgN(3) | 91.40 (6) |
| O—Mg Mg#1 | 40.63 (4) | O#1-Mg-#1 | 40.48 (4) |
| N(1)—Mg—Mg#1 | 133.95 (5) | N(3)—Mg—Mg#1 | 134.23 (6) |
| C(30)—O—Mg | 133.38 (12) | C(30) OMg#1 | 127.08 (12) |
| Mg—O—Mg#1 | 98.89 (6) | N(1)—C(1)—C(2) | 124.4 (2) |
| N(1)—C(1)—C(4) | 120.9 (2) | C(2)—C(1)—C(4) | 114.7 (2) |
| C(1)—N(1)—C(6) | 115.0 (2) | C(1) N(1)—Mg | 119.04 (13) |
| C(6)—N(1)—Mg | 125.87 (12) | C(1)—C(2)—C(3) | 130.1 (2) |
| N(3)—C(3)—C(2) | 125.2 (2) | N(3) C(3)—C(5) | 120.9 (2) |
| C(2)—C(3)—C(5) | 113.9 (2) | C(3)—N(3)—C(18) | 114.7 (2) |
| C(3)—N(3)—Mg | 119.05 (13) | C(18)—N(3)—Mg | 126.14 (12) |
| C(7)—C(6)—C(11) | 120.8 (2) | C(7)—C(6)—N(1) | 118.4 (2) |
| C(11)—C(6)—N(1) | 120.7 (2) | C(8)—C(7)—C(6) | 118.9 (2) |
| C(8)—C(7)C(12) | 119.5 (2) | C(6)—C(7)—C(12) | 121.5 (2) |
| C(7)—C(8)—C(9) | 121.0 (3) | C(10)—C(9)—C(8) | 119.7 (2) |
| C(9)—C(10)—C(11) | 122.1 (3) | C(10)—C(11)—C(6) | 117.5 (2) |
| C(10)—C(11)—C(15) | 119.6 (2) | C(6)—C(11)—C(15) | 122.9 (2) |
| C(7)—C(12)—C(14) | 111.5 (2) | C(7)—C(12)—C(13) | 113.7 (2) |
| C(14)—C(12)—C(13) | 108.7 (2) | C(11)—C(15)—C(17) | 110.6 (2) |
| C(11)—C(15)—C(16) | 113.2 (2) | C(17)—C(15)—C(16) | 109.1 (2) |
| C(19)—C(18)—C(23) | 120.6 (2) | C(19)—C(18)—N(3) | 121.0 (2) |

TABLE 3-continued

Bond lengths [A] and angles [°] for 1.

| | | | |
|---|---|---|---|
| C(23)—C(18)—N(3) | 118.4 (2) | C(20)—C(19)—C(18) | 118.4 (2) |
| C(20)—C(19)—C(21) | 119.0 (2) | C(18)—C(19)—C(24) | 122.6 (2) |
| C(21)—C(20)—C(19) | 121.6 (2) | C(22)—C(21)—C(20) | 119.8 (2) |
| C(21)—C(22)—C(23) | 121.2 (2) | C(22)—C(23)—C(18) | 118.3 (2) |
| C(22)—C(23)—C(27) | 119.7 (2) | C(18)—C(23)—C(27) | 121.9 (2) |
| C(19)—C(21)—C(26) | 110.1 (2) | C(19)—C(24)—C(25) | 113.2 (2) |
| C(26)—C(24)—C(25) | 109.6 (2) | C(23)—C(27)—C(29) | 111.3 (2) |
| C(23)—C(27)—C(28) | 113.6 (2) | C(29)—C(27)—C(28) | 110.7 (2) |
| OC(30)—C(31) | 111.5 (2) | OC(30)—C(32) | 111.2 (2) |
| C(31)—C(30) C(32) | 110.5 (2) | | |

What is claimed is:

1. A complex having the formula I

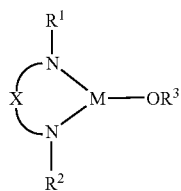

wherein

M is selected from Sn(II), Sn(IV), Al(III) and Mg(II);

each of $R^1$ and $R^2$ is independently hydrocarbyl;

$R^3$ is H or hydrocarbyl; and

X is a carbon containing group, heteroatom or combination thereof.

2. A complex according to claim 1 wherein linker group X comprises a $C_{1-4}$ carbon backbone, or a heteroatom-containing $C_{1-4}$ carbon backbone.

3. A complex according to claim 1 wherein each of $R^1$ and $R^2$ is independently selected from alkyl, cycloalkyl, haloalkyl, aryl, haloaryl or heteroaryl;

$R^3$ is H, alkyl, cycloalkyl, haloalkyl, aryl or haloaryl.

4. A complex according to claim 1 wherein X comprises a vinylene or an arylene group.

5. A complex according to claim 1, having the formula II,

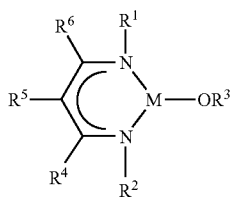

wherein each of $R^4$, $R^5$ and $R^6$ is independently selected from hydrogen, alky, cycloalkyl, haloalkyl, aryl, haloaryl and heteroaryl, and $R^{1-3}$ and M are as defined in claim 1.

6. A complex according to claim 5 wherein each of $R^4$, $R^5$ and $R^6$ is independently selected from H, methyl, t-butyl, phenyl and trifluoromethyl.

7. A complex according to claim 1 wherein M is Sn(II).

8. A complex according to claim 1 having the formula III

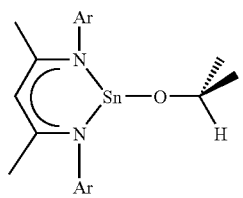

wherein Ar is o-diisopropylphenyl.

9. A complex according to claim 1 wherein M is Mg(II).

10. A complex according to claim 9 having the formula IV

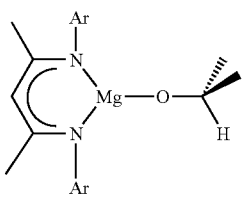

wherein Ar is o-diisopropylphenyl.

11. A complex according to claim 1 having the formula V

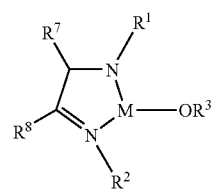

wherein $R^{1-3}$ and M are as defined in claim 1, and wherein each of $R^7$ and $R^8$ is independently selected from H, alkyl, cycloalkyl, haloalkyl, aryl, haloaryl and heteroaryl.

12. A complex according to claim 11 wherein $R^7$ is H and $R^8$ is methyl.

13. A complex according to claim 11 having the formula VI

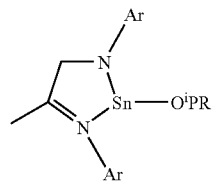

wherein Ar is o-diisopropylphenyl.

14. A complex comprising a dimer of a complex according to claim 1.

15. A dimer according to claim 14 of formula VII

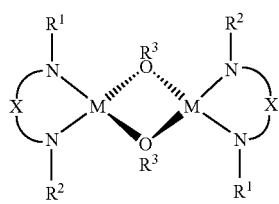

16. A dimer according to claim 14 of formula VIII

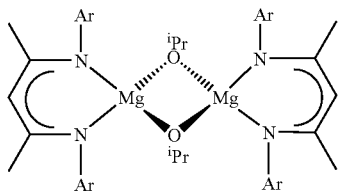

wherein Ar is o-diisopropylphenyl.

17. A method for polymerising a monomer, said method comprising contacting said monomer with an initiator complex having the formula

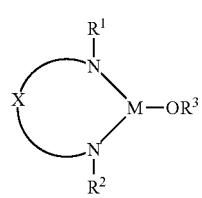

wherein

M is selected from Sn(II), Sn(IV), Al(III) and Mg(II);

each of $R_1$ and $R_2$ is independently hydrocarbyl;

$R_3$ is H or hydrocarbyl; and

X is a carbon containing group, heteroatom or combination thereof.

18. The method according to claim 17 wherein said monomer comprises lactide.

19. The method according to claim 18 wherein the lactide comprises rac-lactide.

20. A process for the polymerisation of lactide, said process comprising contacting an initiating amount of a complex according to claim 1 with a lactide monomer in the presence of a suitable solvent.

21. A process according to claim 20 wherein the ratio of lactide monomer to the complex is between 100:1 and 20000:1.

22. A compound prepared by a process for the polymerisation of lactide, said process comprising contacting an initiating amount of a complex according to claim 1 with a lactide monomer in the presence of a suitable solvent.

23. A medical device comprised of the compound of claim 22.

24. A composition comprising lactide monomer and a complex according claim 1.

25. A composition comprising poly(lactide) and a complex according to claim 1.

26. A composition comprising poly(lactide) and a complex according to claim 1, wherein said complex is deactivated, for example, by the addition of methanol.

27. A process for preparing a complex of formula I, said process comprising the steps of:

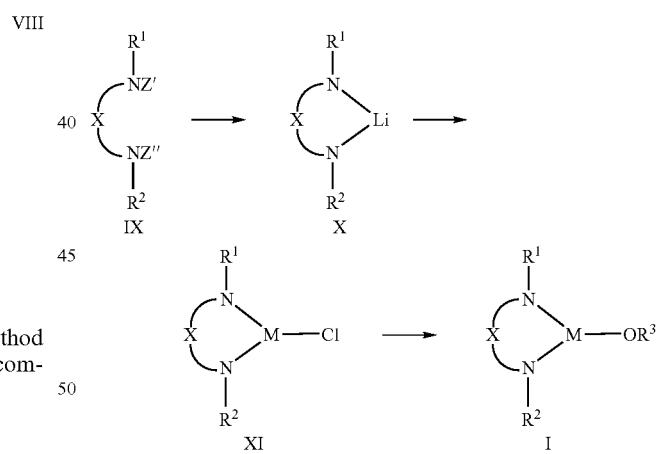

(i) reacting a compound of formula IX, wherein each of Z' and Z" is independently H (where —$NR^1$ and/or —$NR^2$ is an amino group) or absent (where —$NR^1$ and/or —$NR^2$ is an imino group), with $^n$BuLi to form a compound of formula X;

(ii) reacting said compound of formula X with $MCl_n$ to form a compound of formula XI, wherein M is selected from Sn(II), Mg(II), Al(III) and Sn(IV) and n is 2, 2, 3 or 4 respectively;

(ii) reacting said compound of formula XI with $LiOR^3$ to form a complex of formula I;

wherein X and $R^{1-3}$ are as defined in claim 1.

28. A process for preparing a complex of formula XIII, said process comprising the steps of:

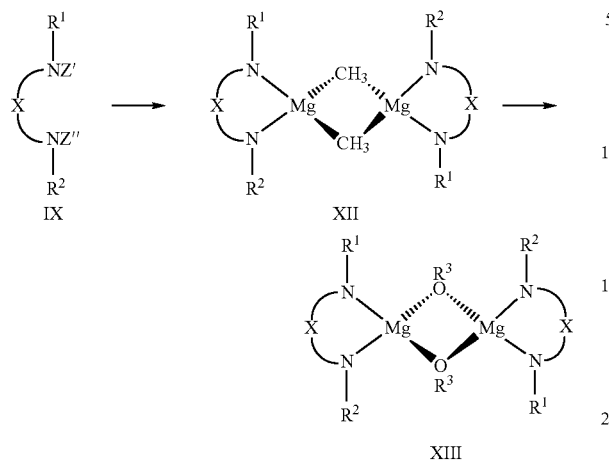

(i) reacting a compound of formula IX, wherein each of Z' and Z" is independently H (where —NR$^1$ and/or —NR$^2$ is an amino group) or absent (where —NR$^1$ and/or —NR$^2$ is an imino group), with MgMe$_2$ to form a compound of formula XII;

(ii) reacting said compound of formula XII with R$^3$OH to form a compound of formula XIII;

wherein X and R$^{1-3}$ are as defined in claim 1.

29. A process for preparing a complex of formula XIII, said process comprising the steps of:

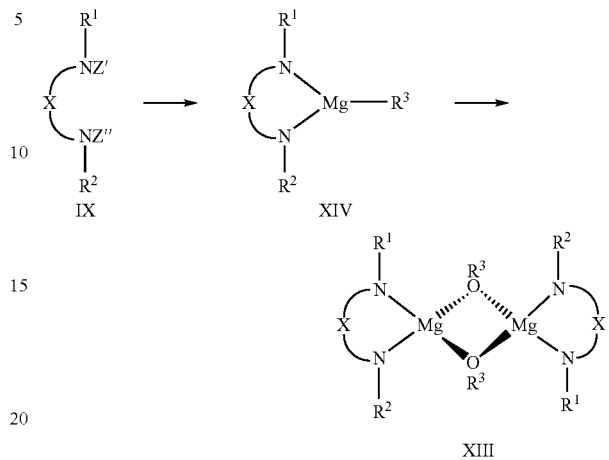

(i) reacting a compound of formula IX, wherein each of Z' and Z" is independently H (where —NR$^1$ and/or —NR$^2$ is an amino group) or absent (where —NR$^1$ and/or —NR$^2$ is an imino group), with (a) "BuLi and (b) R$^3$MgCl to form a compound of formula XIV;

(ii) reacting said compound of formula XIV with O$_2$ to form a complex of formula XIII;

wherein X and R$^{1-3}$ are as defined in claim 1.

* * * * *